United States Patent [19]

Creasman et al.

[11] Patent Number: 5,182,053
[45] Date of Patent: Jan. 26, 1993

[54] PROCESS FOR FORMING INTRAOCULAR LENSES HAVING HAPTICS WITH HIGH FRACTURE TOUGHNESS

[75] Inventors: Edwin A. Creasman, Fontana; Thomas R. Paul, Westlake Village; Kenneth E. Weber, Pacific Palisades; David R. Navarrete, Cerritos; Jimmy D. McCullough, Chino; Churchai T. Soodjinda, West Covina, all of Calif.

[73] Assignee: Optical Radiation Corporation, Azusa, Calif.

[21] Appl. No.: 662,762

[22] Filed: Feb. 28, 1991

Related U.S. Application Data

[63] Continuation-in-part of Ser. No. 789,212, Mar. 2, 1990, Pat. No. 5,037,435.

[51] Int. Cl.⁵ .............................................. B29D 11/00
[52] U.S. Cl. .................................... 264/1.4; 264/1.7; 264/2.7; 264/23
[58] Field of Search .................... 264/1.4, 1.7, 23, 2.7

[56] References Cited

U.S. PATENT DOCUMENTS

| | | | |
|---|---|---|---|
| 3,454,332 | 7/1969 | Siegel | 264/1.7 |
| 4,622,184 | 11/1986 | Barnhart et al. | 264/1.7 |
| 4,638,025 | 1/1987 | Fuhrman | 524/40 |
| 4,737,322 | 4/1988 | Bruns | 264/1.7 |

FOREIGN PATENT DOCUMENTS

| | | | |
|---|---|---|---|
| 136809 | 8/1979 | Fed. Rep. of Germany | 264/23 |
| 135333 | 6/1987 | Japan | 264/23 |
| 135334 | 6/1987 | Japan | 264/23 |
| 249717 | 10/1987 | Japan | 264/23 |

OTHER PUBLICATIONS

*Plastics World*, "Use of Ultrasonic Vibrations in Resin Compounding and Casting", Black et al., Feb. 1963, pp. 26–27 (264/23).

*Primary Examiner*—James Lowe
*Attorney, Agent, or Firm*—Christie, Parker & Hale

[57] ABSTRACT

A process for forming an intraocular lens with haptics having high fracture toughness mixing solid particles with an uncured polymer matrix and introducing the uncured mixture into a mold. Ultrasonic energy is then applied to the mold until the uncured mixture begins to solidify. Sufficient heat is then applied to the polymer mixture to completely cure the polymer. The cured polymer which will form the haptics, is then removed from the mold and a hole for forming the optic is formed in the cured polymer. An uncured polymer matrix suitable for use, when cured, as an optic, is then introduced into the hole and cured. An intraocular lens is then machined from the resulting cured composition.

9 Claims, 1 Drawing Sheet

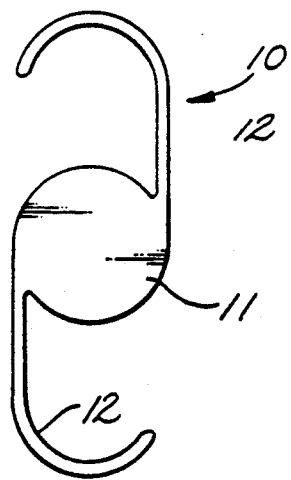 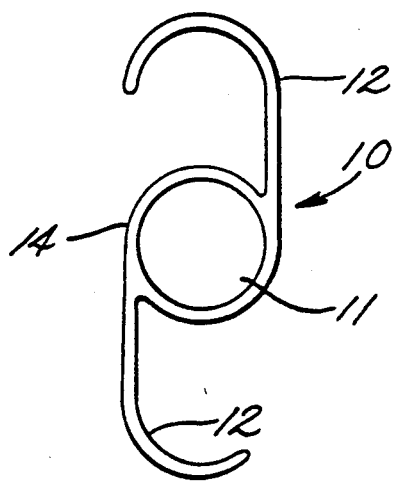

PROCESS FOR FORMING INTRAOCULAR LENSES HAVING HAPTICS WITH HIGH FRACTURE TOUGHNESS

This is a continuation-in-part of U.S. patent application Ser. No. 07/489,212, filed Mar. 2, 1990, now U.S. Pat. No. 5,037,435, issued Aug. 6, 1991.

FIELD OF THE INVENTION

This invention relates to intraocular lenses for the human eye, and more particularly to a one-piece intraocular lens including haptics having high fracture toughness.

BACKGROUND OF THE INVENTION

The replacement of a natural lens with an artificial intraocular lens implant in the human eye has become a well known procedure to physicians specializing in ophthalmology. In such a procedure, a corneo-scleral incision is made in the eye through which the natural lens is removed and the artificial intraocular lens is inserted. The intraocular lens may be designed to be positioned within either the anterior or posterior chamber of the eye.

Intraocular lenses typically include a central lens section, referred to as the optic, for focusing light onto the retina. One or more supporting structures, called haptics, extend outwardly from the optic to align and stabilize the optic with respect to the pupil. Typically the haptics comprise one or more filamentous or wire-like arms or loops which extend radially outwardly from the periphery of the optic. The haptics may be fixed in position within the eye by sutures or by engagement with predetermined eye tissues.

Installation of an intraocular lens should be permanent so that subsequent surgical adjustments are not required. Accordingly, the reliability of the haptic is of great importance. The materials of construction and the design parameters must be selected such that the haptic can endure significant stresses with minimum risk of breakage. Moreover, the haptic must be capable of functioning safely in the presence of small stress risers, such as notches or nicks, which may be inflicted during handling and manipulation.

Unfortunately, haptics often develop clusters of fractures, referred to as craze, when subjected to impact and bending forces during handling. If the individual craze fractures are large enough to extend across a significant portion of the shaft diameter, a broken haptic results.

For intraocular lens haptics, there is concern that inadvertent impacts and stresses encountered in service may result in the development of relatively large craze flaws which could eventually lead to failure. Even if breakage does not occur, the existence of sizeable craze fractures that may extend to the surface of the haptic would be of concern from a biocompatibility point of view.

SUMMARY OF THE INVENTION

Accordingly, this invention provides haptics for intraocular lenses having high fracture toughness, i.e. which are resistant to the formation of large craze fractures. The haptics are formed from a polymer composition comprising a polymer matrix with a relatively low concentration of small, solid particles dispersed throughout the polymer matrix. The solid particles are present in an amount of up to about 1.0% by weight, a preferably present in an amount of from about 0.05% to about 0.5% by weight.

The size of the particles is preferably not more than about 5 microns and is preferably from about 0.1 to about 0.8 micron. The solid particles are of materials which are biocompatible. The presently preferred solid particles are of copper phthalocyanate and titanium dioxide. Cooper phthalocyanate is particularly preferred because it imparts a blue color to the haptic as well as toughening the haptic against crazing.

The polymer matrix preferably comprises poly(methyl methacrylate) (PMMA) and a cross-linking agent, preferably ethylene glycol dimethacrylate (EGDMA).

In a preferred embodiment of the invention, there is provided a one-piece intraocular lens comprising a clear optic and a pair of filamentous, colored haptics having high fracture toughness.

The present invention further provides a process for preparing a polymer composition having high fracture toughness comprising cured polymer matrix and solid particles dispersed throughout the polymer matrix for use in construction of the haptics. The process comprises mixing the solid particles with uncured components of the polymer matrix to form an uncured polymer mixture. The uncured polymer mixture is then introduced into a mold and ultrasonic energy is applied to the mold and mixture for a time sufficient for the uncured mixture to solidify. Curing of the composition is then completed under conventional conditions, e.g., the application of heat, and the cured polymer composition is then removed from the mold.

In a preferred process, the mixture of solid particles and uncured components of the polymer matrix are subjected to ultrasonic energy to disperse the solid particles within the mixture before the mixture is introduced into the mold. Thereafter, ultrasonic energy is applied to the mold and mixture contained therein for a time sufficient for the mixture to partially cure and solidify.

In a particularly preferred embodiment of the invention, dispersion of the solid particles is enhanced by first removing electrostatic charges from the solid particles and preferably also from the mold. This is done through the use of commercially available antistatic equipment. Alternatively, a small amount of an antistatic chemical agent such as an electrically conductive salt, e.g. a quaternary ammonium salt, may be added to the solid particles. Thereafter, the solid particles are mixed with the uncured components of the polymer matrix and ultrasonic energy is applied to the mixture to disperse the solid particles within the mixture. The mixture is then introduced into a mold for curing and ultrasonic energy is applied to the mold and mixture contained therein for a time sufficient for the mixture to partially cure and solidify. Thereafter, heat is applied to the mold and contained mixture until curing is complete.

BRIEF DESCRIPTION OF THE DRAWINGS

These and other features and advantages of the present invention will be better understood by reference to the following detailed description when considered in conjunction with the accompanying drawings wherein:

FIG. 1 is a top view of a preferred intraocular lens constructed in accordance with the present invention; and FIG. 2 is a top view of another preferred intraocular lens.

DETAILED DESCRIPTION

A preferred one-piece posterior chamber intraocular lens constructed in accordance with the present invention is shown in FIG. 1. The intraocular lens 10 comprises a generally circular optic 11 and a pair of filamentous haptics 12. In the embodiment shown, the optic has a diameter of about 7 mm and the haptics have a cross-sectional diameter of about 0.13 to about 0.26 inch along most of their length. It is understood that the dimensions may vary as desired.

The haptics 12 are made of a first polymer composition comprising a first polymer matrix and a relatively low concentration of discrete solid particles generally uniformly dispersed throughout the first polymer matrix.

The solid particles have a particle size of up to about 5 microns and are preferably in the range of about 0.1 to about 0.8 microns. In general, smaller particles are preferred over larger particles. Particles having a size greater than about 5 microns are not preferred because such particles tend to create large fractures when the haptic is placed under stress and thus tend to reduce the strength and flexibility of the haptics.

Particles having a size less than about 0.8 microns are particularly preferred because, in the preferred loadings, such particles have been found to result in the greatest resistance to the formation of large, stress-induced fractures. The solid particles tend to act as inhibitors to the curing of the polymer matrix. Slow curing tends to increase the flexibility of the polymer matrix. This beneficial effect is enhanced by the presence of smaller particles, such as those having a particle size less than about 0.8 microns.

Particles having a size less than about 0.1 microns are not presently preferred because they are generally commercially unavailable and also because they tend to be more difficult to disperse uniformly throughout the polymer matrix.

The solid particles are present in the first polymer matrix in a positive amount of up to about 1.0% by weight and are preferably present in an amount of from about 0.05% to about 0.5% by weight. Loadings above 1.0% are not preferred because the particles tend to agglomerate and precipitate or drop out of suspension during the curing of the first polymer matrix. Haptics comprising solid particles in the preferred size range and loadings in the range of from about 0.05% to about 0.5% have been found to exhibit the greatest degree of resistance to the formation of large fractures.

The solid particles may be made of any biocompatible material, i.e., one that is inert and non-toxic to the fluids of the eye, which will not dissolve in the uncured monomers that polymerize to form the polymer matrix, and which form a discrete solid phase in the cured polymer matrix. The presently preferred solid particles are made of copper phthalocyanate. Copper phthalocyanate is preferred because it is biocompatible and because it is colored, i.e. blue, thus introducing all the benefits of a colored material to the haptic. For example, colored haptics are easier to see and therefore manipulate during surgery.

It is understood, however, that any biocompatible solid particles may be used. Examples of other suitable materials include titanium dioxide, fumed silica, barium sulfate and other highly insoluble and inert materials. Carbon black may be used but is not presently preferred because it tends to be difficult to disperse into uniform discrete particles, i.e. carbon black tends to agglomerate into chains. Particles of elastomeric materials, e.g., polybutadiene, polyethylene, etc., may also be used provided that such elastomeric materials are biocompatible.

While not being bound by theory, it is believed that the toughening, i.e., resistance to the formation of large fractures, imparted to the haptic material by the presence of the solid particles is the result of stress-induced nucleation of multiple subsurface fracture sites at the locations of the solid particles. The subsurface fracture sites are believed to retard the growth of larger fractures by relieving stress in regions of greatest stress concentration. It is also believed that the absorption of mechanical impact energy associated with the formation of the sizeable surface area contained within the subsurface fracture sites may promote toughening.

It is believed that the preferred sizes and loadings of the solid particles, as indicated above, provide the optimum particle size and spacing of particles, when uniformly dispersed throughout the polymer matrix, to minimize overlap of the subsurface fractures created at each particle site when the haptic is placed under bending stress.

Also, as indicated above, the addition of the solid particles tends to retard the polymerization of the polymer matrix. This could result in a more flexible, less cross-linked envelope around each particle. Such a layer or envelope would be more elastic than the surrounding cured resin and could contribute to stress relief by providing increased plastic deformation capability.

The optic 11 is made of a second polymer composition comprising a second polymer matrix and is preferably clear, i.e. free of any coloring agents. It is preferred that the first and second polymer matrices be the same. If different, the monomers of the first polymer which polymerize to form the first and second polymer matrices are preferably able to cross-link or polymerize with each other to form an integral one-piece structure.

As used herein, "one-piece" refers to a construction wherein the optic and haptic comprise polymeric matrices, which, when cured in contact with each other, will copolymerize or cross-link to form a strong chemical bond with each other to form an integral unit.

The first and second polymer matrices may comprise any suitable medical grade polymers that are and non-toxic to the fluids of the eye and which impart sufficient strength and rigidity to the haptics to support the optic 11 within the eye. Suitable polymers may be derived from acrylate monomers including methyl acrylate, ethyl acrylate, butyl acrylate and isodecyl acrylate, methacrylate monomers such as methyl methacrylate, ethyl methacrylate, n-hexyl methacrylate, butyl methacrylate and vinyl acetate monomers and appropriate mixtures thereof as is well known in the art. A polymer matrix comprising poly(methyl methacrylate) (PMMA) is presently preferred for the optic and haptics.

As indicated above, it is preferred that the intraocular lens comprise a clear optic and colored haptics. In such an arrangement, it is preferred that there be a sharp demarcation between the colored portions of the lens and the clear portions. Such a sharp boundary enables consistent optic and haptic dimensions to be achieved.

Accordingly, it is preferred that one or both of the first and second polymer matrixes contain a cross-linking agent. If no cross-linking agent is used, unpolymerized monomers in one polymer matrix tend to dissolve polymerized monomers of the other matrix at the interface between the two, leading to a slight migration of the solid particles and a "fuzziness" at the boundary. If a cross-linking agent is present in either of the polymer matrices, this is prevented. Also, if the haptic material contains a dye, the cross-linking agent tends to prevent the dye from leaching into the optic.

Any suitable cross-linking agent may be used. Difunctional monomers such as ethylene glycol dimethacrylate (EGDMA), ethylene glycol diacrylate, triethylene glycol dimethacrylate (TEGDMA), triethylene glycol diacrylate, allyl methacrylate (AMA), allylacrylate, polyethylene glycol dimethacrylate (PEGDMA), polyethylene glycol diacrylate, 1,3-butylene glycol dimethacrylate (BGDMA), 1,3-butylene glycol diacrylate, 1,4-butylene glycol dimethacryalte (BGDMA), 1,4-butylene glycol diacrylate, diethylene glycol dimethacrylate (DEGDMA), diethylene glycol diacrylate, 1,6-hexanediol dimethacrylate (HDODMA), 1,6-hexanediol diacrylate, neopentyl glycol dimethacrylate (NPGDMA), neopentyl glycol diacrylate, tripropylene glycol dimethacrylate (TPGDMA) and tripropylene glycol diacrylate (TPGDA), difunctional and trifunctional monomers such as trimethylolpropane trimethacrylate and trimethylolpropane triacrylate are presently preferred.

In addition to providing the cross-linking function, the above cross-linking agents act as dispersants, helping to evenly distribute the particles throughout the mixture. It is understood that dispersants other than the crosslinking agents mentioned above may be used. However, it is preferred that the dispersants cross-link with monomers so that they will not leach out after the intraocular lens is implanted in the eye.

A suitable catalyst such as 2.2° azobis [2-methylpropanenitrile] (AIBN) or benzoyl peroxide (BPO) is used to initiate polymerization.

If desired, the haptics 12 may comprise one or more pigments to either impart color to or enhance the color of the haptics. Suitable pigments include dyes which are compatible with the first polymer matrix, such as DuPont 2050 blue dye, BASF Neozapon blue 807, BASF Heliogen blue L6875F, Sandoz Chemicals Savinyl blue RLS, Milliken Chemicals Reactint blue X3 and Sun Chemicals phthalo blue C48-5411. While not preferred, it is understood that the second polymer composition which forms the optic may comprise a dye, if desired.

The presently preferred first polymer composition which forms the haptics comprises a first polymer matrix including about 95% by weight PMMA, about 5% by weight EGDMA, about 0.05% by weight AIBN and about 0.05% by weight copper phthalocyanate having a particle size of from about 0.1 to about 0.8 microns uniformly dispersed throughout the first polymer matrix. Such a composition exhibits a tensile strength of about 10,000 psi and an elongation of greater than 10% as well as enhanced resistance to large fracture formation.

The presently preferred second polymer composition which forms the optic comprises a second polymer matrix including about 95% by weight PMMA, about 5% by weight ultraviolet (UV) absorber, and about 0.05% by weight BPO. It is understood that, while preferred, the presence of a UV absorber is not required for the practice of the invention. Suitable ultraviolet absorbers are described, for example, in U.S. Pat. No. 4,636,212 to Posin, which is incorporated herein by reference.

Referring again to FIG. 1, the optic 11 shown is generally circular and plano-convex. However, noncircular and biconvex or meniscus, i.e. concave-convex, optics may be used if desired. The diameter of the optic may also vary as desired. Diameters of about 6 and about 7 millimeters are presently preferred.

The haptics 12 shown in FIG. 1 comprise a pair of curved, filamentous or wire-like structures which extends in opposite directions from opposite sides of the optic 11. Each haptic 12 first extends in a direction generally tangential to the optic and then curves to generally track the curvature of the optic 11.

It is understood, however, that the number, size, shape and position of the haptics may vary as desired. Moreover, the haptics may have free ends as shown in FIG. 1 or may form a loop and may be co-planar with the optic 11 or at or at selected angle relative to the optic 11.

Other suitable haptic arrangements which can be used in the practice of the present invention in which the haptics have a free end are shown, for example, in U.S. Pat. Nos. 4,575,374 to Anis, 4,589,147 to Nevyas, 4,591,358 to Kelman, 4,601,720 to Sinsky, 4,601,721 to Kamerling, 4,504,981 to Walman, 4,476,591 to Arnott and 4,435,855 to Pannu, all of which are incorporated herein by reference. If desired, the free end of the haptic may be enlarged and comprise a suture or manipulation hole, e.g., as shown in U.S. Pat. Nos. 4,575,374, to Anis, 4,476,591 to Arnott and 4,435,855 to Pannu, which are incorporated herein by reference.

Exemplary haptic arrangements which can be used in the practice of the present invention wherein the haptics form loops are shown in U.S. Pat. Nos. 4,502,163 to Graham, 4,588,405 to Knolle, Jr, 4,502,162 to Gerhard et al. and 4,110,848 to Jensen, all of which are incorporated herein by reference.

With reference to FIG. 2, the optic 11 may be surrounded by a circumferential sheath 14 of the first polymer composition. Such a circumferential sheath 14 increases the interface area between the first and second polymer compositions which form the haptics 12 and optic 11 respectively. This, in turn, enhances the bond strength between the first and second polymer compositions.

It has been found that conventional mechanical mixing techniques do not provide adequate dispersement of the solid particles in the polymer matrix and do not provide a means for maintaining dispersement of the particles during initial stages of the curing process before solidification occurs. With conventional techniques, the particles tend to agglomerate and settle out before the polymer matrix solidifies in the mold. Accordingly, the present invention further comprises a process for providing a uniform dispersement of the solid particles within the first polymer matrix.

The process comprises mixing the solid particles with the uncured polymer matrix components, i.e., unpolymerized or partially polymerized monomers, and then subjecting the uncured polymer mixture to ultrasonic energy during the initial curing of the polymer matrix, i.e., until the polymer matrix solidifies within a mold. This can be done, for example, by immersing the mold containing uncured polymer matrix into an ultrasonic bath. After the polymer matrix solidifies, further curing can be conducted without the application of ultrasonic energy.

The uncured polymer mixture may be first subjected to mechanical agitation and then to ultrasonic energy to disperse the solid particles in the uncured polymer mixture before the mixture is introduced into the mold. Application of ultrasonic energy is continued while the mixture solidifies in the mold. Thereafter, curing can be completed without ultrasonic energy.

Dispersement of the solid particles may be further enhanced by eliminating, or at least reducing, static electrical charges on the solid particles prior to mixing the solid particles with the uncured polymer components. This can be done, for example, by introducing the solid particles into the ion stream generated by any suitable commercially available antistatic device.

In such a process, it is also preferred to treat the mold to eliminate, or at least reduce, static electrical charges on the surface of the mold. This is done, e.g., by the use of a deionizing air gun or any other suitable available antistatic device. Elimination of static charges reduces the electrical attraction between the particles and between the particles and the walls of the mold. This, in turn, reduced agglomeration of the particles as well as settling of the particles against the mold walls.

In a preferred embodiment of the process uncured polymer mixture which will form the haptics is cast around a rigid rod or pin. The pin is preferably made of metal with 13, 15 or 17 series stainless steel being particularly preferred. In such an embodiment, the rigid pin is centered, e.g. with slotted centering washers in a tube made out of glass, plastic or other suitable material. The centering washers can be made out of teflon, a corrosion resistant non-toxic metal or the like. The diameter of the pin is the same as the diameter of the optic and the inner diameter of the tube is at least as large as a circle circumscribing the haptics.

The uncured haptic polymer mixture is poured through the slots of the centering washers into the annular space surrounding the pin. The tube is then sealed and placed in an ultrasonic bath until the polymer mixture begins to solidify. The tube is then removed, cooled and allowed to completely cure. The hardened polymer matrix is then removed from the tube and the pin removed from the hardened polymer matrix. Before the pin is removed, it is preferred to turn the rod in a lathe using the pin as the turning center. This establishes high concentricity between the exterior surface of the rod and interior surface, i.e. the surface of the axial hole formed by the pin.

The axial hole in the rod is filled with uncured polymer mixture which will form the optic which is then allowed to cure. The resultant solid rod having a central optic region and outer haptic region can then be sliced into disks for further processing into finished IOLs.

The casing of haptic material around a rigid pin offers several advantages. For example, it saves the labor and cost of drilling an axial hole in the formed rod as well as monitoring the accuracy and quality of the drilled hole. It also provides a hole having a smoother wall than that typically achieved by drilling. This latter feature results in a finished intraocular lens having a sharper, more cosmetically pleasing optic-haptic interface and a more consistent interface with respect to physical properties.

By using the pin as a turning center to achieve a high degree of concentricity between the surface of the hole after pin removal and the outer surface of the rod, the resultant intraocular lens has a higher degree of concentricity between the optic and haptic regions. This is particularly noticeable in those intraocular lens constructions comprising a circular optic surrounded by a ring of haptic material as shown in FIG. 2.

It is understood that the mold in which the first polymer matrix is allowed to cure may be of any desired shape or design. For example, molds which provide plates or sheets of the cured material, as well as rods or buttons, may be used. It is understood that molds which provide thicker sections may require cooling of the material after removal from the ultrasonic bath to prevent overheating of the material during curing.

To manufacture an intraocular lens from the cured material, if the first polymer matrix material is not cast around a pin or the like, a circular hole having a diameter the same as the desired diameter of the optic is cut or drilled in the cured polymer, i.e. in the sheet, rod, button or the like which is formed. The hole is then filled with uncured second polymer matrix material and allowed to cure. This results in a composite structure in the form of a solid sheet, rod, button or the like comprising a clear center or circular region of second polymer matrix, from which the optic is formed, surrounded by first polymer matrix, preferably colored, from which the haptics are formed. The composite structure is then cut or cored as required, and the haptics are then formed by conventional machining techniques.

EXAMPLE I

Approximately 0.1 grams of copper phthalocyanate received from BASF having a specified particle size of 0.1 to 0.8 micron was vacuum dried in a deionized breaker overnight at room temperature and $27 \pm 1$ inches Hg.

94.89 grams of distilled methyl methacrylate (MMA), 5.0 grams EGDMA and 0.05 grams AIBN were weighed and combined in an Erlenmeyer flask and then mixed for 20 minutes in a lab top stirrer using a stir bar.

An amount of the vacuum dried copper phthalocyanate slightly greater than 0.0625 grams was placed in a porcelain dish and then inside an antistatic container which was transported to an antistatic treatment station. The antistatic treatment station consisted of a commercially available antistatic device marketed as Simco ME Shockless Static Bar 7KV RMS Work Patent No. 3,120,626.

The porcelain dish containing the copper phthalocyanate was placed in the antistatic field and stirred or agitated for approximately 5 minutes using a porcelain spatula. The porcelain dish was then placed back into the antistatic container for transport to a weighing station. 0.0625 grams of the antistatic treated copper phthalocyanate was weighed out and combined with the MMA, EGDMA and AIBN in the Erlenmeyer flask.

The resulting mixture was then stirred for 30 minutes on a lab top stirrer using a stir bar. The stirred mixture was then placed in a 40 KHz ultrasonic bath for two hours at $48° \pm 2°$ C. The bath contained a surfactant to optimize ultrasonic activity.

The mold cavity or haptic cell into which the mixture was poured consisted of a pair of glass sheets and a gasket which extends generally around the perimeter of the glass sheets clamped between the glass sheets. The glass sheets were cleaned thoroughly and deionized using a deionizing air nozzle. The cell was then assembled, clamping the gasket between the glass sheets. The gasket had a seal which could be opened to allow the introduction of the polymer mixture into the cell.

Under an antistatic laminar flow hood, the gasket seal is opened and the inside of the cell is deionized with a deionizing air gun. A funnel is also deionized in the same manner. The funnel is then placed in the gasket seal opening. The Erlenmeyer flask containing the polymer mixture is removed from the ultrasonic bath and the cell is filled with the polymer mixture. The cell is then sealed and clamped. A secondary seal of tape is placed around the cell.

The haptic cell is then immediately immersed in the 40 KHz ultrasonic bath which had been degassed for 2 hours and stabilized at 50°+1, −3° C. The cell is immersed in the ultrasonic bath for 25-35 minutes until the polymer mixture has solidified.

The cell is then removed from the bath, dried and placed in a curing oven at 115°±10° overnight. The cell is then placed in an oven at 265° F. for 4 hours and then placed in a holding oven at 190° F. until the cell is opened. A sheet of polymer material in which the copper phthalocyanate particles are uniformly dispersed results.

To form intraocular lenses from the sheet, holes, having a diameter of about 6 mm were drilled in the sheet and an uncured composition containing 65% MMA and 35% C-400, which is a polymer powder comprising MMA and an ultraviolet light absorber made by Optical Radiation Corporation of Azuza, Calif., was poured into and filled the holes. The sheets having holes containing the uncured material were heated to about 170° F. for about 4 hours, and then to about 220° F.±10 for another 2 hours. A solid sheet having clear PMMA centers surrounded by the blue PMMA haptic material resulted.

The sheet was then cut to form buttons having a clear center surrounded by a blue annular ring. The buttons were then lathe cut and mill cut to obtain intraocular lenses having a clear optic and a pair of blue haptics having high fracture toughness.

It is apparent that many alterations and changes in the above described compositions and procedures can be practical without meaningfully departing from the principles, spirit and scope of this invention. For example, it is apparent that, if a one-piece construction is not desired, haptics may simply be cut or formed from the cured first polymer matrix material and attached to an optic by conventional methods, e.g., heat staking or the like.

Accordingly, the foregoing description should not be read as pertaining only to the precise compositions and procedures described, but rather should be read consistent with and as support for the following claims which are to have their fullest fair scope.

EXAMPLE II

Copper phthalocyanate blue pigment is vacuum dried in a deionized beaker overnight at 120° F. and 27±1 inches of mercury.

The total batch weight for production is determined and distilled methylmethacrylate (MMA), EGDMA and AIBN were weighed out per the following guidelines:

EGDMA=5.0% of total batch weight
AIBN=0.025% of total batch weight
Copper phthalocyanate=0.0625% of total batch weight
MMA=remainder of total batch weight The MMA, EGDMA and AIBN is then weighed and combined in an Erlenmeyer flask. These components are mixed for 20 minutes on a lab top stirrer using a stir bar. The solution is filtered through a 0.6 micron filter.

An amount of vacuum dried copper phthalocyanate slightly larger than the required amount is placed in a porcelain dish and then inside an antistatic container for transportation to an antistatic treatment station. The copper phthalocyanate is then placed in an antistatic field and manipulated for approximately 5 minutes with a porcelain spatula. The copper phthalocyanate is then placed back in the antistatic container for transportation to a weighing station.

The calculated amount of copper phthalocyanate is then weighed out on an analytical balance and the antistatic treatment is repeated. The treated, weighed copper phthalocyanate is then combined with the MMA, EGDMA and AIBN in the Erlenmeyer flask. The solution is then mixed for approximately 30 minutes on a lab top stirrer using a stir bar.

The mixed solution is then placed in a 40 KHz ultrasonic bath for one and one half to two hours at 51° C. ±3° C. The bath contains a surfactant to optimize the ultrasonic activity.

A pyrex glass test tube, 25×200 mm is cleaned thoroughly and deionized with nitrogen. A stainless steel pin having an appropriate diameter, e.g. 6 mm, and having TEFLON (tetrafluoroethylene resins) centering spacers on the top and bottom, is then inserted into the pyrex glass tube which is then purged with nitrogen and covered to keep clean. The mixture of MMA, EGDMA, AIBN and copper phthalocyanate is then poured into the test tube until it is full. The test tube is then covered with a Wheaton cap and teflon plumber's tape is then applied around the cap to assure an airtight seal.

The sealed test tube is then placed in a 40 KHz ultrasonic bath for one and one half to two hours at 50° C. -56° C. The polymer is checked for curing after one and one half hours. Once polymerization begins, the polymer is checked approximately once each minute until the mixture has solidified. When solidified, the test tube is placed in a cold water batch at approximately 40° F. for 30-60 minutes. The tube is then transported to a circulated water bath for 20 hours at 36° C.±1° C. The temperature of the water bath is then raised to 45° C. for an additional 4 hours. The tube is then transported to a post cure oven at 265° F. for approximately 4 to 5 hours. The tube is then cooled to 150° F. and removed from the oven.

A cured polymerized rod is removed from the glass test tube and inspected for defects. The polymerized rod is then turned and sized on a lathe using the metal pin as the turning center. The metal pin is then removed and the polymerized rod having an axial hole is annealed at 200° F. in an annealing oven and then cooled slowly to 140° F. The polymerized rod is then removed from the annealing oven.

The axial hole in the polymerized rod is cleaned thoroughly with a solvent. The outside of the rod is then covered with tape for protection from the optic resin. The axial hole is plugged at one end and a resin reservoir is attached to the opposite end of the rod. The hole is purged with nitrogen and then filled with an uncured resin which forms the optic of the intraocular lens. The uncured resin comprises 65% MMA and 35% C-400.

The rod containing uncured optic resin is then degassed for 15 to 20 minutes at 24-25 inches mercury vacuum to remove any bubbles in the optic resin. The resin reservoir is then covered with TEFLON (tetrafluoroethylene resins) tape to prevent contamination of the optic resin. The rods are then placed in an oven for curing of the optic resin at 125° F.±5° F. for 42 hours. The tape is then removed and the oven temperature is increased to 210° F.±10° F. and continued at 210° F. for 2 hours. The rods were then cooled to 140° F. and removed from the oven.

The rods were then sliced to the desired thickness to form buttons which were then lathe cut and mill cut to obtain the desired intraocular lenses.

What is claimed is:

1. A process for preparing an intraocular lens having haptics with high fracture toughness comprising:
    mixing uncured first polymer matrix and solid particles to form a curable first polymer composition;
    introducing the curable first polymer composition into a mold cavity;
    applying ultrasonic energy to the mold and the curable first polymer composition contained therein for a time sufficient for the curable first polymer composition to solidify;
    applying sufficient heat to the first polymer composition to complete curing of the first polymer composition to form a first molded construction;
    removing the first molded construction from the mold;
    forming a hole in the first molded constructions;
    filling the hole with a curable second polymer composition comprising uncured second polymer matrix;
    curing the second polymer composition to thereby form a cured polymer final construction comprising a region of cured second polymer composition surrounded by cured first polymer composition; and
    forming an intraocular lens from the cured polymer final construction.

2. A process as claimed in claim 1 wherein the mold cavity provides a first molded construction in the shape of a sheet.

3. A process as claimed in claim 1 wherein the mold cavity provides a first molded construction in the shape of a rod.

4. A process as claimed in claim 1 wherein the mold cavity provides a first molded construction in the shape of a disk.

5. A process as claimed in claim 1 further comprising, prior to introducing the curable first polymer composition into the mold cavity, applying ultrasonic energy to the curable first polymer composition to disperse the solid particles throughout the first polymer matrix.

6. A process as claimed in claim 1 further comprising, prior to mixing the solid particles and first polymer matrix, removing static charges from the solid particles.

7. A process as claimed in claim 1 further comprising, prior to introducing the curable first polymer composition into the mold cavity, removing static charges from the mold.

8. A process for preparing an intraocular lens having haptics with high fracture toughness comprising:
    providing a cylindrical mold comprising a rigid pin and an annular space surrounding the rigid pin;
    mixing uncured first polymer matrix and solid particles to form a curable first polymer composition;
    introducing the first polymer composition into the annular space of the mold surrounding the rigid pin;
    applying ultrasonic energy to the mold and first polymer composition contained therein for a time sufficient for the curable first polymer composition to solidify;
    applying sufficient heat to the first polymer composition to complete curing of the first polymer composition to form a first molded construction;
    removing the first molded construction from the mold cavity;
    removing the pin from the first molded construction to provide a hole;
    filling the hole in the first molded construction with a curable second polymer composition comprising uncured second polymer matrix;
    curing the second polymer composition to thereby form a cured polymer final construction comprising a center region of cured second polymer composition and an outer annular region of cured first polymer composition; and
    forming at least one intraocular lens from the cured polymer final construction.

9. A process as claimed in claim 8 further comprising, prior to removing the pin, turning and sizing the first molded construction on a lathe using the pin as the turning center.

* * * * *

UNITED STATES PATENT AND TRADEMARK OFFICE
CERTIFICATE OF CORRECTION

PATENT NO. : 5,182,053         Page 1 of 2

DATED      : January 26, 1993

INVENTOR(S): E.A. Creasman; T.R. Paul; K.E. Weber;
             D.R. Navarrete; J.D. McCullough; C.T. Soodjinda It is certified that error appears in the above-identified patent and that said Letters Patent is hereby corrected as shown below:

On the title page: Item

[63] Related U.S. Application Data, change "789,212" to
     -- 489,212 --.

OTHER PUBLICATIONS, line 2, change "Feb." to -- March --.

Abstract, line 2, after "toughness" insert -- comprises --.

Column 2, line 1, change "a" to -- and --.
Column 2, line 2, before "present" insert -- are --.
Column 2, line 9, change "Cooper" to -- Copper --.

Column 4, line 49, after "that are" insert -- inert --.

Column 5, line 18, change "dimethacryalte" to
     -- dimethacrylate --.
Column 5, line 33, change "crosslinking" to
     -- cross-linking --.
Column 5, line 37, change "2.2°" to -- 2.2' --.

Column 6, lines 10,11, change "extends" to -- extend --.
Column 6, line 19, after "optic 11" change "or at or at" to
     -- or at a --.

Column 8, line 44, after "Work" insert a comma.
Column 8, line 57, change "KHz" to -- kHz --.

UNITED STATES PATENT AND TRADEMARK OFFICE
CERTIFICATE OF CORRECTION

PATENT NO. : 5,182,053

DATED : January 26, 1993

INVENTOR(S) : E.A. Creasman; T.R. Paul; K.E. Weber;
D.R. Navarrete; J.D. McCullough; C.T. Soodjinda It is certified that error appears in the above-identified patent and that said Letters Patent is hereby corrected as shown below:

Column 9, line 11, change "KHz" to -- kHz --.
Column 9, line 27, change "Azuza" to -- Azusa --.
Column 9, lines 48-52, move this paragraph to column 11, and insert between lines 10 and 11:

-- Accordingly, the foregoing description should not be read as pertaining only to the precise compositions and procedures described, but rather should be read consistent with and a support for the following claims which are to have their fullest fair scope. --

Column 10, line 19, change "KHz" to -- kHz --.
Column 10, line 23, after "mm" insert a comma.
Column 10, line 32, after "teflon" insert -- (tetrafluoroethylene resins) --.
Column 10, line 35, change "KHz" to -- kHz --.

Signed and Sealed this

First Day of March, 1994

*Attest:*

BRUCE LEHMAN

*Attesting Officer*    Commissioner of Patents and Trademarks